(12) United States Patent
Roukes et al.

(10) Patent No.: US 7,959,873 B1
(45) Date of Patent: Jun. 14, 2011

(54) BIOLOGICAL DETECTION BASED ON DIFFERENTIALLY COUPLED NANOMECHANICAL SYSTEMS USING SELF-SENSING CANTILEVERS WITH ATTONEWTON FORCE RESOLUTION

(75) Inventors: Michael Roukes, Pasadena, CA (US);
Hongxing Tang, Pasadena, CA (US);
Jessica Arlett, S Pasadena, CA (US);
James Maloney, Pasadena, CA (US);
Benjamin Gudlewski, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 1111 days.

(21) Appl. No.: 11/491,394

(22) Filed: Jul. 20, 2006

Related U.S. Application Data

(60) Provisional application No. 60/701,714, filed on Jul. 21, 2005, provisional application No. 60/781,986, filed on Mar. 14, 2006.

(51) Int. Cl.
*G01N 33/00* (2006.01)
(52) U.S. Cl. ..... 422/400; 422/402; 422/68.1; 422/82.05
(58) Field of Classification Search ............. 422/50, 422/57, 58, 55, 68.1, 82.05, 99, 400, 402, 422/82.01
See application file for complete search history.

(56) References Cited

U.S. PATENT DOCUMENTS

| | | | |
|---|---|---|---|
| 5,780,304 A | | 7/1998 | Matzinger |
| 6,016,686 A | * | 1/2000 | Thundat ................. 73/23.2 |
| 6,096,559 A | * | 8/2000 | Thundat et al. ............. 436/147 |
| 6,602,469 B1 | | 8/2003 | Maus |
| 6,805,839 B2 | * | 10/2004 | Cunningham et al. ..... 422/82.12 |
| 7,560,070 B1 | * | 7/2009 | Baller et al. ................ 422/50 |
| 2003/0027351 A1 | * | 2/2003 | Manalis et al. ............. 436/165 |

* cited by examiner

*Primary Examiner* — Sam P Siefke
(74) *Attorney, Agent, or Firm* — Marcus C. Dawes; Daniel L. Dawes

(57) ABSTRACT

A biosensor is comprised of a free and a biofunctionalized recognition self-sensing nanocantilever, a dock adjacent to the ends of the nanocantilevers, and a gap between the nanocantilevers and dock. The self-sensing cantilevers each include a semiconductor piezoresistor defined in a pair of legs about which the cantilevers flex. A bias power or current is applied to the piezoresistor. The sensitivity of the cantilevers is optimized for a given ambient temperature and geometry of the cantilevers and dock by minimizing the force spectral density, $S_F$, of the cantilevers to determine the optimum bias power, $P_{in}$. A sub-aN/√Hz force sensitivity is obtained by scaling down the dimensions of the cantilevers and supplying an optimum bias power as a function of temperature and geometry.

5 Claims, 10 Drawing Sheets

FIG. 1

BIOLOGICAL DETECTION BASED ON DIFFERENTIALLY COUPLED NANOMECHANICAL SYSTEMS USING SELF-SENSING CANTILEVERS WITH ATTONEWTON FORCE RESOLUTION

RELATED APPLICATIONS

The present application is related to U.S. Provisional Patent Application Ser. No. 60/701,714, filed on Jul. 21, 2005, and 60/781,986, file on Mar. 14, 2006, both of which are incorporated herein by reference and to which priority is claimed pursuant to 35 USC 119.

GOVERNMENT RIGHTS

The invention was developed using funds from National Science Foundation, contract ECS-0089061, and from the NAVY SPAWAR Systems Center, contract N66001-02-1-8914. The U.S. Government has certain rights.

BACKGROUND OF THE INVENTION

1. Field of the Invention

The invention relates to the field of self-sensing piezoresistive nanocantilevers used as biosensors and methods of optimized biasing self-sensing piezoresistive nanocantilevers.

2. Description of the Prior Art

Silicon microscale and, more recently, nanoscale cantilevers enable important applications such as atomic force microscopy (AFM) and biological force spectroscopy. Most efforts in this area employ cantilever probes with external displacement transduction via off-chip sensing systems. These systems are typically optically-based, involving simple optical beam deflection or more sensitive interferometry. Self-sensing cantilevers, which possess integrated displacement transducers, offer important advantages that are not attainable with external optical methods. Perhaps most prominent are: scalability to extremely small cantilever dimensions (far below an optical wavelength) and, thereby, to very high frequencies; measurement without optical perturbation of susceptible samples; suitability for large-array technologies and portable sensing; and ease of applicability to multiple-cantilever sensors that permit correlated or stochastic detection. Furthermore, use of on-chip electronic readout is especially advantageous for detection in liquid environments of low or arbitrarily varying optical transparency, as well as for operation at cryogenic temperatures where maintenance of precise optical component alignment becomes problematic.

Emerging forefront applications such as magnetic resonance force microscopy (MRFM) of single spins, and BioNEMS (biofunctionalized NEMS) for single-molecule biosensing; require compliant mechanical nanosensors with force sensitivity at the thermodynamic limit. A milestone along the path towards ultralow noise, self-sensing devices is the work of Harley and Kenny who demonstrated piezoresistive microcantilevers achieving a force noise spectral density of 8.6 $fN/\sqrt{Hz}$ in air at a frequency of about 1 kHz with extremely compliant, 30 pN/m devices. More recently, Bargatin et al. report measurements of piezoresistive nanocantilevers operating at very high frequencies, up to about 71 MHz, attaining a force sensitivity of 350 $aN/\sqrt{Hz}$ in vacuum at room temperature.

Nanoelectromechanical systems (NEMS) have advantages of matching the biological system both in size and in speed. However, it is not a simple task to observe the biological signals from these sensors. Due to the ultra-small size of the nanoscale sensors, the signal generated by individual nanosensor is generally exceedingly small. This tiny signal is also vulnerable to the large parasitic signal from the electrochemical environment.

BRIEF SUMMARY OF THE INVENTION

The illustrated embodiment comprises at least one and preferably a nanoelectromechanical sensor suite or pair of micro or nanocantilevers that utilizes a docking configuration to quench the motion of nanomechanical cantilevers or sensors when a biological target is bound between them and a dock. Differential signal detection is employed to reduce common-mode signal due to the environment in which the sensor resides. Molecular or pathogen binding or biotarget binding can be monitored in real time at high precision.

In the illustrated embodiment actuation of the NEMS is greatly simplified. Individually addressing of each sensor unit is not required in the illustrated embodiment. Simple, remote or global actuation such as by a thermal, fluidic and piezoelectric method can be employed on a much larger scale. This also makes the sensor suite essentially scalable. A large sensor array containing hundreds of such suites can further improve the signal-to-noise ratio.

In general, thin, piezoresistive silicon cantilevers have been shown to provide unprecedented sensitivity for force detection in an integrated, self-sensing, readily-scalable configuration. The devices realized in the illustrated embodiment are patterned from single-crystal Si epilayer membranes utilizing conventional bulk micro- and nano-machining processes. The illustrated embodiment demonstrates an electrically transduced force sensitivity of 235 $aN/\sqrt{Hz}$ at room temperature and 17 $aN/\sqrt{Hz}$ at 10° K. Enhancement of the p+ piezoresistive gauge factor is observed at cryogenic temperatures. The performance of the illustrated embodiment elucidates the ultimate, low-temperature sensitivity attainable from self-sensing nanoelectromechanical systems (NEMS) utilizing displacement transduction based upon semiconducting piezoresistors.

In the illustrated embodiment we demonstrate self-sensing cantilevers with greatly improved sensitivity, and, for the first time, the ultimate limits to the performance of such devices that can be expected at low temperatures where thermal noise is small is explored. In addition to studying the temperature dependence and force sensitivity of such devices, we characterize the piezoresistive gauge factor, G, for silicon from cryogenic to room temperature. Previous studies of the piezoresistive gauge factor have focused upon just a few temperatures or solely explored the range above 50K.

The small cantilevers of the illustrated embodiment employ high sensitivity piezoresistive strain sensing based upon an integrated semiconducting epilayer. This embodiment of electrical displacement transduction opens a wide parameter space permitting ultra-small scale, very low stiffness, and very high frequency devices, a regime not approachable via conventional optical detection. This transduction method is also well-suited for scaled-down versions of complex detection schemes, such as that of Chui et al., which enables independent resolution of both vertical and lateral forces. (THIS IS NOT WELL DISCLOSED AND LATERAL FORCE DETECTION DOES NOT SEEM TO BE ENABLED HERE)

The illustrated embodiment of the invention is also a method of fabrication for membrane-derived piezoresistive cantilevers based upon bulk micro- and nano-machining processes. We provide an experimental and theoretical evaluation of their performance.

Thus, the illustrated embodiment of the invention can be characterized as an apparatus comprising at least one self-sensing micro or nanocantilever having a movable distal end; and at least one dock adjacent to the distal end, the dock and the distal end arranged and configured to bind to a biotarget extending between the distal end and the dock.

In the preferred embodiment there are at least two substantially identical self-sensing micro or nanocantilevers each having a movable distal end and a dock adjacent to corresponding distal ends. One of the two distal ends arranged and configured to bind to the biotarget extending between the one distal end and the dock. A differential detector coupled to the at least two self-sensing micro or nanocantilevers to provide an output signal with common mode rejection. A remote actuator is provided to actuate the self-sensing micro or nanocantilevers, particular when a plurality of such paired self-sensing micro or nanocantilevers are configured into an array.

Alternatively, the illustrated embodiment can be characterized as comprising a self-sensing free nanocantilevers, a self-sensing biofunctionalized recognition nanocantilevers, a rigid dock adjacent to the free and recognition nanocantilevers, a gap of predetermined size defined between the free and recognition nanocantilevers and the dock, a differential detector coupled to the self-sensing free and recognition nanocantilevers, and a global actuator of the free and recognition nanocantilevers. The global actuator comprises a source of a microfluidic force applied to the cantilevers, a thermal actuator, or a piezoelectric actuator. In one embodiment the predetermined size of the gap is of the order of microns to sub-100 nm.

In the preferred embodiment each free and recognition nanocantilever has a distal end and where a pair of notches are defined in the dock, the distal ends of the free and recognition nanocantilevers extending into corresponding ones of the pair of notches defined in the dock to form a C-shape for the gap. A cantilever perimeter adjacent to the gap of the distal end of the recognition nanocantilever and a gap perimeter adjacent to the gap of the corresponding notch defined in the dock further comprise a metallic pattern disposed on the cantilever and gap perimeters which is biofunctionalized. The gap between the dock and the free cantilever is larger than the gap between the dock and the recognition cantilever by an amount to substantially prevent pathogen binding between the free cantilever and dock.

In another embodiment the free and recognition cantilevers have dimensions of the order of microns to sub-100 nm.

The self-sensing free nanocantilevers and self-sensing biofunctionalized recognition nanocantilevers each comprise a semiconductor piezoresistor for self-sensing defined in a pair of legs about which the cantilevers flex, and the differential detector comprises a source of bias power applied to the piezoresistor. The sensitivity of the cantilevers is optimized for a given ambient temperature and geometry of the cantilevers and dock by minimizing the force spectral density, $S_F$, of the cantilevers to determine the optimum bias power, $P_{in}$. $S_F$ is given by $$S_F = S_F^{\gamma} + S_F^{J} = \frac{2k_B K_0}{\pi f_0 Q} \int_0^{l_{leg}} \frac{T_{ph}}{l_{leg}} dy + \frac{4k_B R_T}{F^2} \int_0^{l_{leg}} \frac{T_{ph}}{l_{leg}} dy$$

where $S_F^{\gamma}$ is the thermomechanical noise, $S_F^{J} = S_V^{J}/\Im^2$ is the (Johnson) electrical noise (RTI), $K_B$ is the Boltzman constant, $K_0$ is the force constant for the cantilevers, $f_0$ is the fundamental resonant frequency of the cantilevers, $l_{leg}$ is the length of the legs of the cantilevers, Q is the quality factor of the cantilevers, $\Im = \Re(Q/K_0)$ is the ganged system responsivity, the product of the transducer and on-resonance mechanical responsivities, and $S_V^{J} = 4k_B T_h R_T$ is the (Johnson) voltage noise of the transducers, $R_T$ is the resistance of the "sensing region", $T_{ph}$ is the effective temperature of the phonons, and $T_h$ is the effective temperature of the holes.

In still another embodiment the force sensitivity, $\sqrt{S_F}$, of the cantilevers is minimized to a force noise floor of not more than 17 aN/√Hz at approximately 10K. In any case, a sub-aN/√Hz force sensitivity is obtained by scaling down the dimensions of the cantilevers and supplying an optimum bias power as a function of temperature and geometry.

The invention is also characterized as an improvement in a method of operating a self-sensing micro or nanocantilever including a semiconductor piezoresistor defined in at least one leg about which the cantilever flexes to obtain optimum force sensitivity $\sqrt{S_F}$ comprising applying an amount of bias power or current to the piezoresistor at a given ambient temperature and geometry of the cantilever at which bias power or current the force spectral density, $S_F$, of the cantilever is minimized.

The spectral force density $S_F$ which exhibits a minimum as a function of bias power or current is given by the equation set forth above. In one embodiment the force sensitivity, $\sqrt{S_F}$, of the cantilevers is minimized to a force noise floor of not more than 17 aN/√Hz at approximately 10K. However, sub-aN/√Hz force sensitivity is obtained by scaling down the dimensions of the cantilevers and supplying a bias power or current as a function of temperature and geometry at which bias power or current force sensitivity exhibits a minimum.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

BRIEF DESCRIPTION OF THE DRAWINGS

FIG. 1 is a perspective diagram of two pairs of cantilevers according to the illustrated embodiment of the invention.

FIG. 8a is a graph showing the effective phonon temperature [K] dependent performance of the resonance frequency of the nanocantilever force sensor of FIG. 7a.

FIG. 8b is a graph showing the effective phonon temperature [K] dependent performance of the quality factor of the nanocantilever force sensor of FIG. 7a.

FIGS. 11a and 11d are graphs of an evaluation of the bias power dependence of the effective force noise for the two device geometries. FIGS. 11b and 11e are graphs of an effective temperature as a function of ambient temperature for the two device geometries. FIGS. 11c and 11f are graphs of the optimum force sensitivity as a function of ambient temperature for the two device geometries.

FIGS. 11a and 11d are graphs of an evaluation of the bias power dependence of the effective force noise.

FIGS. 11a and 11d are graphs of an evaluation of the bias power dependence of the effective force noise.

Figure 2A:
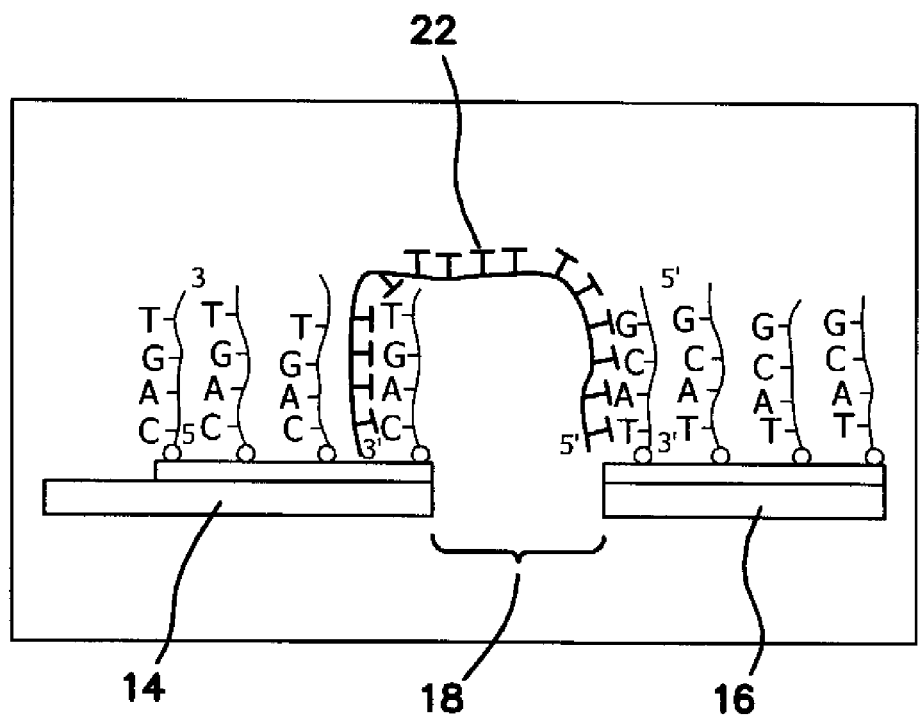
FIG. 2a is a diagrammatic side view of the recognition cantilever selectively functionalized to bind RNA/ssDNA.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

Figure 1:
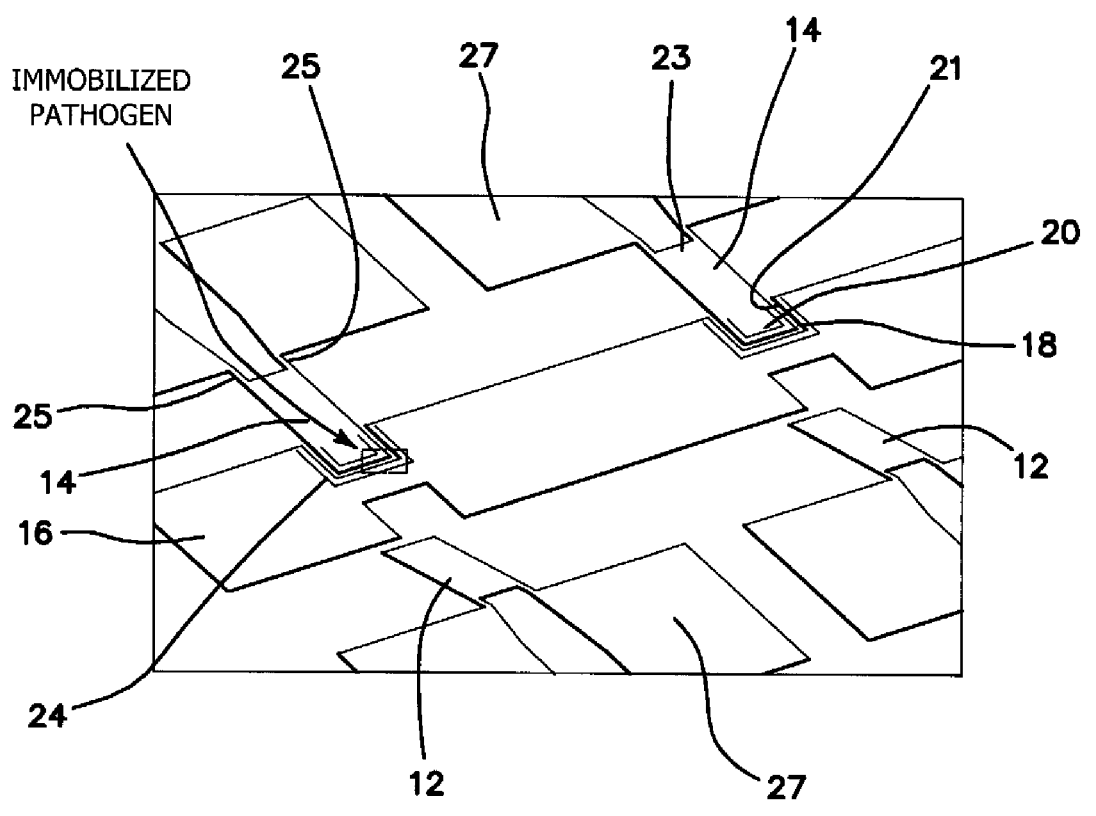

The disclosed detection system 10 is illustrated in FIG. 1 and is comprised of three mechanical components fabricated using conventional nanoelectromachining of silicon (NEMS): a free or reference cantilever 12; a functionalized recognition cantilever 14; and a rigid dock 16. Free cantilever 12 and recognition cantilever 14 are designed to have same geometry and to yield an identical transduction signal if driven simultaneously. Cantilevers 12 and 14 extend from their proximal ends 23 by one or more, preferably two flexures 25 integrally formed with support 27. The dock 16 is a mechanically rigid part that remains stationary under global actuation. A small gap 18 is etched between the dock and the cantilevers 12 and 14. The gap size varies from the order of microns to sub-100 nm. The movable distal ends 20 of cantilevers 12 and 14 extends into a mating notch 21 defined in fixed dock 16, but is separated from dock 16 by a gap 18.

The gap 18 between the dock 16 and cantilever 14 is intended to bind a biological target across it. When such a binding event happens, either a biomolecule or a pathogen, dependent on the size of the gap 18, the cantilever 14 motion is constrained to the dock 16. The cantilever 12, designed to be a free cantilever, provides reference signal. The transduction difference from cantilevers 12 and 14 will reflect the presence of the biological target.

This differential signal comes from the different design in cantilever 14 and its reference cantilever 12. Depending on the implementation of this difference, this sensor suite can be used both as a specific and nonspecific biosensor.

Figure 2B:
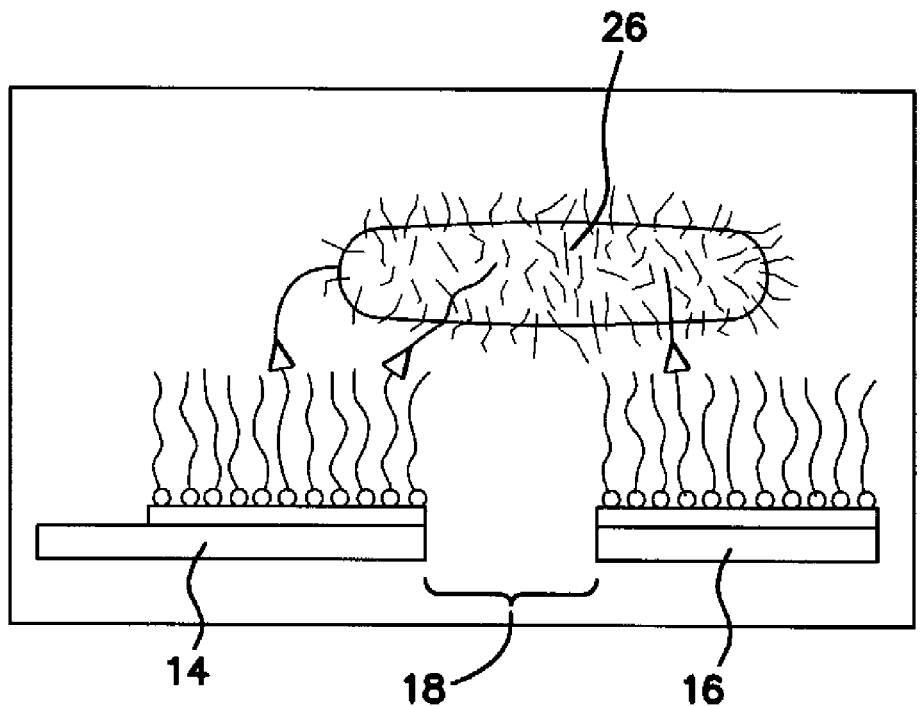
FIG. 2b is a diagrammatic side view of the recognition cantilever selectively functionalized to bind a pathogen.

The device depicted in FIG. 1 is a specific biosensor. The recognition cantilever 14 is different from cantilever 12 in that it is a functional device. A thin gold pattern 24 formed as an "e" shape or a pair of nested "C's" is defined at the perimeter end 20 of the cantilever 14 and on the closest adjacent perimeter of dock 16 as shown in FIG. 2a. This area or pattern 24 of gold can be biofunctionized. There are many approaches to form a biofunctionized surface on gold pad 24. For example, a self-assembled monolayer (SAM) can be used to modify the gold surface 24 only to link biomolecules (such as ssDNA or RNA) or antibodies. FIG. 2a shows an example of a RNA molecular 22 linking the cantilever 14 and the dock 16. To avoid the formation of an RNA loop, the dock 16 and the cantilever gold pads 24 have to been prefunctionized with a different sequence of nucleotides to match two ends of the target RNA. FIG. 2b exemplifies a pathogen 26 (e-coli) linking to the dock 16 and cantilever 14. Both cantilever 14 and dock gold surfaces are pre-functionalized with anti-E. coli antibodies.

Figure 3:
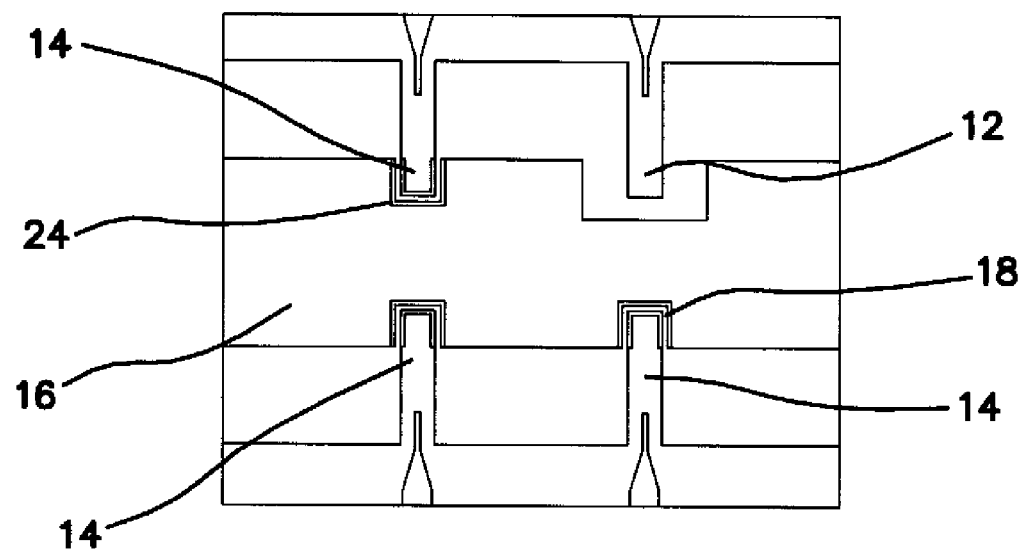
FIG. 3 is a top plan view of a geometrically differentiated nonspecific pathogenetic detector.

The docking scheme explained in FIG. 1 can also be utilized as a non-specific biological detector/counter. This is achieved by appropriate geometric design in the reference cantilever 14. FIG. 3. illustrates such a cantilever system. In this embodiment, the gap 18 between the recognition cantilever 14 and the dock 16 is comparable to the size of target pathogen. While there is a large gap between the reference cantilever 12 and the dock 16 to ensure substantially no binding happens between the reference or free cantilever 12 and the dock 16. This free cantilever 12 resides in a similar fluidic environment and can provide a proper reference signal to the cantilever 14 when its binding happens.

Turn now to signal detection and a measurement scheme. Detection is achieved via piezoresistive effect of the construction material of the nanomechanical system. Doped silicon is such an example. The devices shown in FIG. 3 are actually made of epitaxially grown p+ Si. The two legs 28 that support the cantilevers 12 and 14 provide a return path for a sensing electrical current. The legs 28 are made extremely narrow to concentrate strain and to maximize the piezoresistive effect. In response to the, stress applied upon the cantilever 12 or 14, the resistance across the legs 28 varies slightly and can be detected through measurement electronics.

Figure 4:
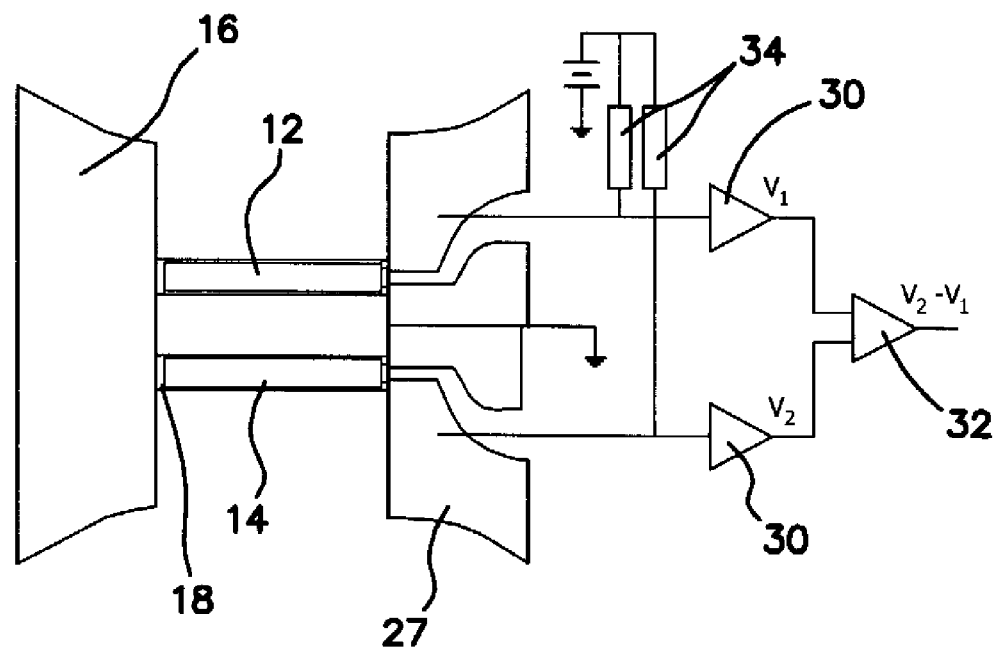
FIG. 4 is an equivalent schematic for the recognition and reference cantilever of FIGS. 1-3.

In order to compensate the large environmental background noise and provide a differential signal between the reference cantilever 12 and recognition cantilever 14, the two cantilevers 12, 14 are incorporated into two arms 34 of a Wheatstone bridge with identical sensing current passing through both cantilevers 12, 14 as shown in the schematic of FIG. 4. The signal from each arm 34 is coupled to one of the two high impedance amplifiers 30. Their difference is measured through another differential amplifier 32 to remove the background "common-mode" noise and obtain high gain.

Turn now to the actuation schemes. The docking sensor suite does not require actuation of each individual cantilever 12, 14. This greatly simplifies the actuation which is usually extremely challenging in nanomechanical systems. For example, any on of three illustrated actuation schemes that can drive the recognition and reference cantilevers 12, 14 simultaneously and let them to provide differential signal when target is bound are contemplated within the scope of the invention. First, there is a microfluidics drive mechanism. When a nanomechanical device is embedded in a microfluidics system, the moving fluid around the device can apply a force to the nanomechanical device and cause it to move with the fluid. The motion of the fluid can be modulated by alternating pressure to the microfluidics or a microfluidic pump in its close proximity. This driving mechanism is strong and can provide an actuation force as large as several nN force to the nanoscale cantilevers.

Figure 5:
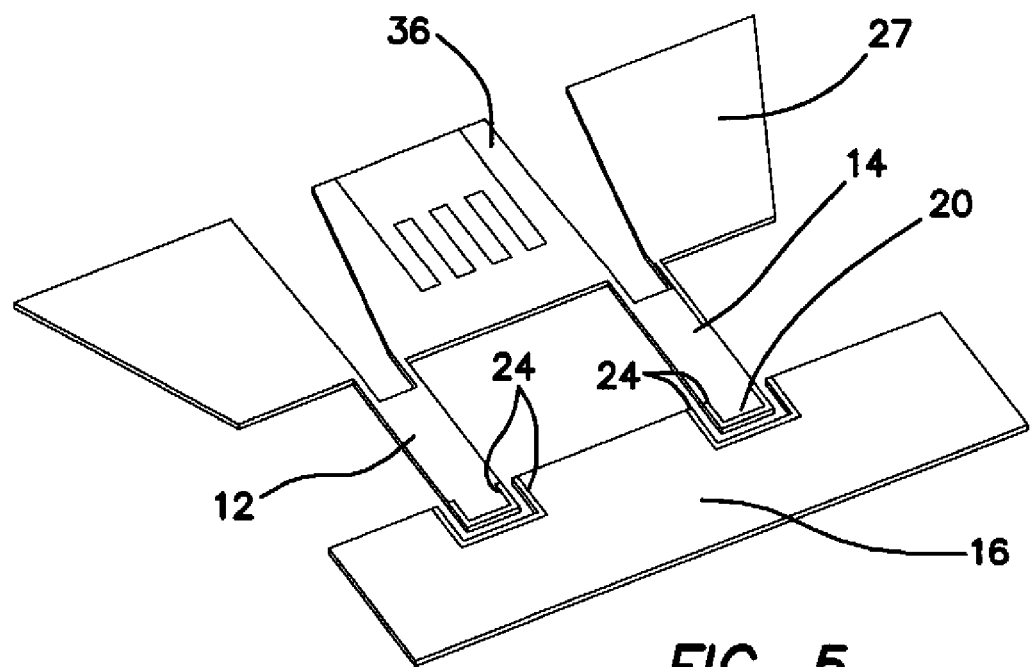
FIG. 5 is a perspective view of a diagram illustrating a thermal actuation scheme using a local heater to modulate the temperature of nanomechanical components and to drive them through thermal expansion and contraction.

Second, there is a thermal actuation scheme. This scheme relies on a local heater fabricated on or close to the nanomechanical sensors. Alternating electrical current in the heater will modulate the temperature of the sensor suite therefore cause thermo-expansion or contraction of these mechanical components as illustrated in FIG. 5. A local heater 36 is employed to modulate the temperature of the nanomechanical components and therefore drive them through thermal expansion or contraction.

Third, there is a piezoelectric actuation scheme. Similar to the diagram in FIG. 5, a piezoelectric crystal can be fabricated on shared support structure of reference cantilever 12 and recognition cantilever 14 to provide easy actuation of both cantilevers 12, 14. Piezoelectric actuation is usually very strong and this renders the location of the piezoelectric component noncritical. It could be placed at some distance away from the nanosensors.

Consider now an integrated nanocantilever array for RNA/ssDNR detection. The sensor suite described above can be integrated in parallel or in series to form an array. The benefits are in two aspects. First, the magnitude of the signal can be enhanced by the size of the array. For example, if the number of suites or pairs of cantilevers 12 and 14 in the array is N, the signal amplification, A, is $$A = 20 \log N \text{ (dB)}$$

A gain of 40 dB can be easily achieved by putting 100 sensor suites in series.

Figure 6:
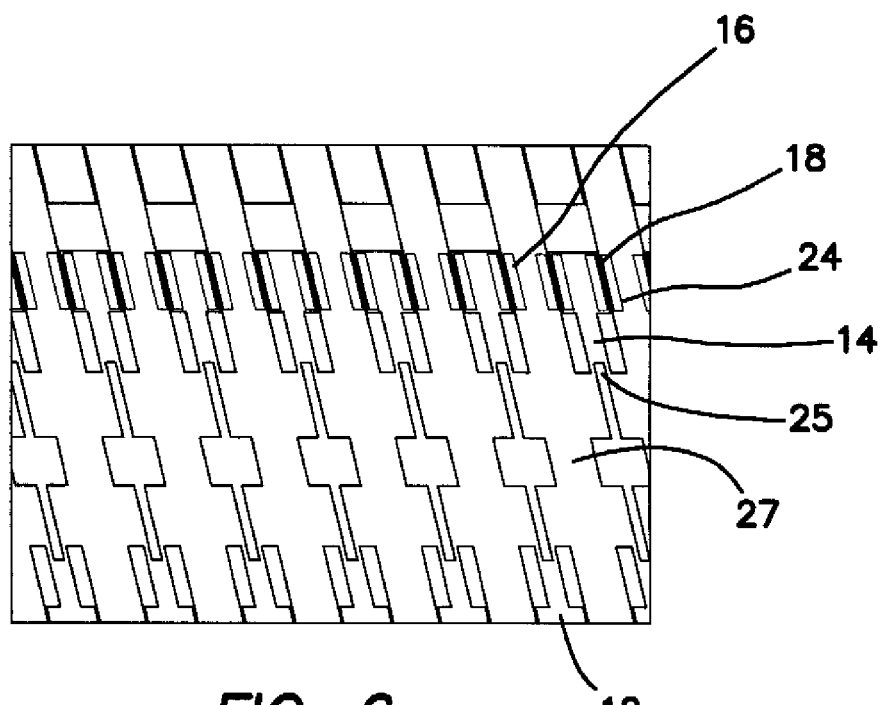
FIG. 6 is microphotograph of an array docking sensor suites of the illustrated embodiment.

Second the effective surface area for accessing biological targets is enhanced by a factor of N as shown in the layout diagram of the array of FIG. 6. This is essential for detecting low concentrations of biomolecules or bacterial matter. In this embodiment cantilevers 12 and 14 have been widened on their proximal ends to form a shovel end on which biofunctionalized gold layer 24 has been deposited on the side edges only. The adjacent fixed dock 16 is in this embodiment a strip disposed between adjacent cantilevers 12 and 14. The strip that forms fixed dock 16 also extends to then act as support 27 to both rows of cantilevers 12 and 14. That portion of dock 16 adjacent to recognition cantilevers 14 is also provided with a biofunctionalized gold layer 24 and gap 18 is then defined between the adjacent biofunctionalized gold layers 24 on dock 16 and cantilever 14. The embodiment of FIG. 6 differs from that of FIG. 1 in that the gap 18 is provided only on the sides of a widened cantilever 12, 14 in FIG. 6, while it is provided in a circumferentially adjacent notch 21 surrounding the distal end 20 of cantilevers 12 and 14 in FIG. 1. Opposing row of cantilevers 14 is a row of similar reference cantilevers 12 partially shown in the lower portion of microphotograph of FIG. 6 and another row of reference cantilevers 12 partially shown in the upper portion of microphotograph of FIG. 6. The rows of reference and recognition cantilevers 12 and 14 are thus alternated in an array as many times as desired. The geometry of the row of cantilevers 12 is identical to that of cantilevers 14 except for the biofunctionalization added to the row of cantilevers 14. The biofunctionalization of each cantilever 14 may differ, may differently be provided on a row-by-row basis or otherwise arbitrarily assigned as may be needed in each application.

Figure 7A:
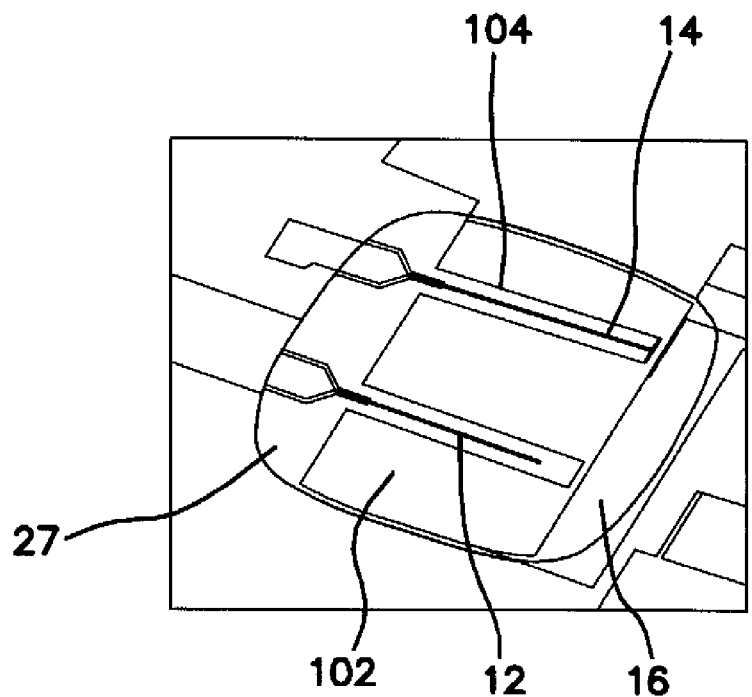
FIG. 7a is a SEM image of the piezoresistive nanocantilever force sensor as used in a microfluidic device.

Consider now a more detailed analysis of the sensitivity of the docked cantilevers in general and not necessarily limited to a biofunctionalized application. A scanning electron microscope [SEM] image of a typical device is shown in FIG. 7a. The cantilevers 100 are situated at the top of a deep-etched "fluidic via" 102 through a substrate 104, an illustrative, but not limiting, configuration which is devised for embedding the devices within microfluidic systems for biosensing applications. In the illustrated embodiment we characterize the cantilevers in vacuo in a temperature range from room to cryogenic temperatures to demonstrate the utility of the devices for ultrasensitive force detection.

Figure 7B:
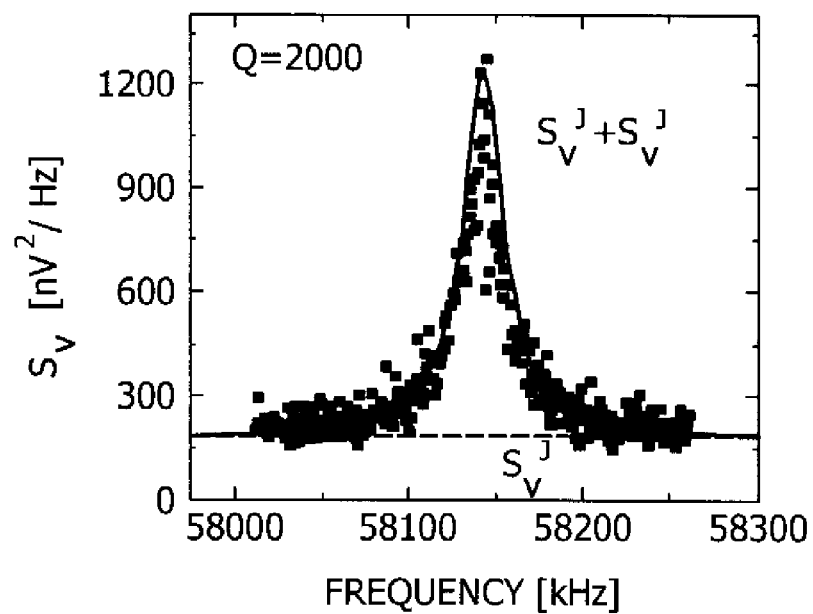
FIG. 7b is a graph of the voltage noise spectral density obtained at room temperature with a 0.3V bias, measured at the device output terminals.
Figure 7C:
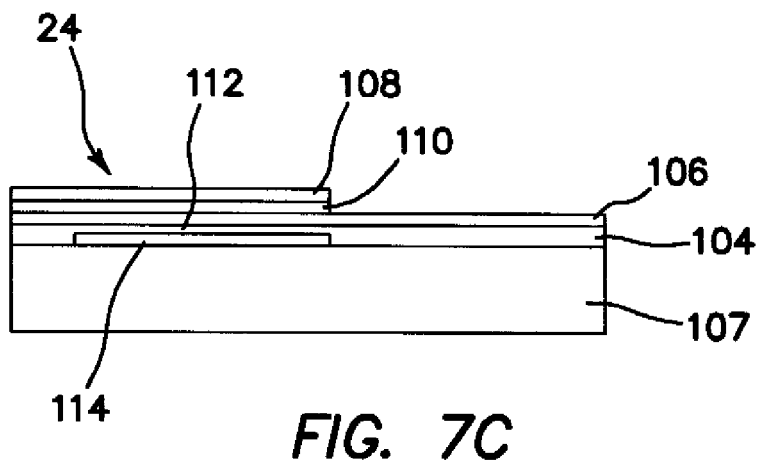
FIG. 7c is a diagrammatic side cross sectional view of the substrate and overlying cantilever shown in an intermediate stage of fabrication.
Figure 10:
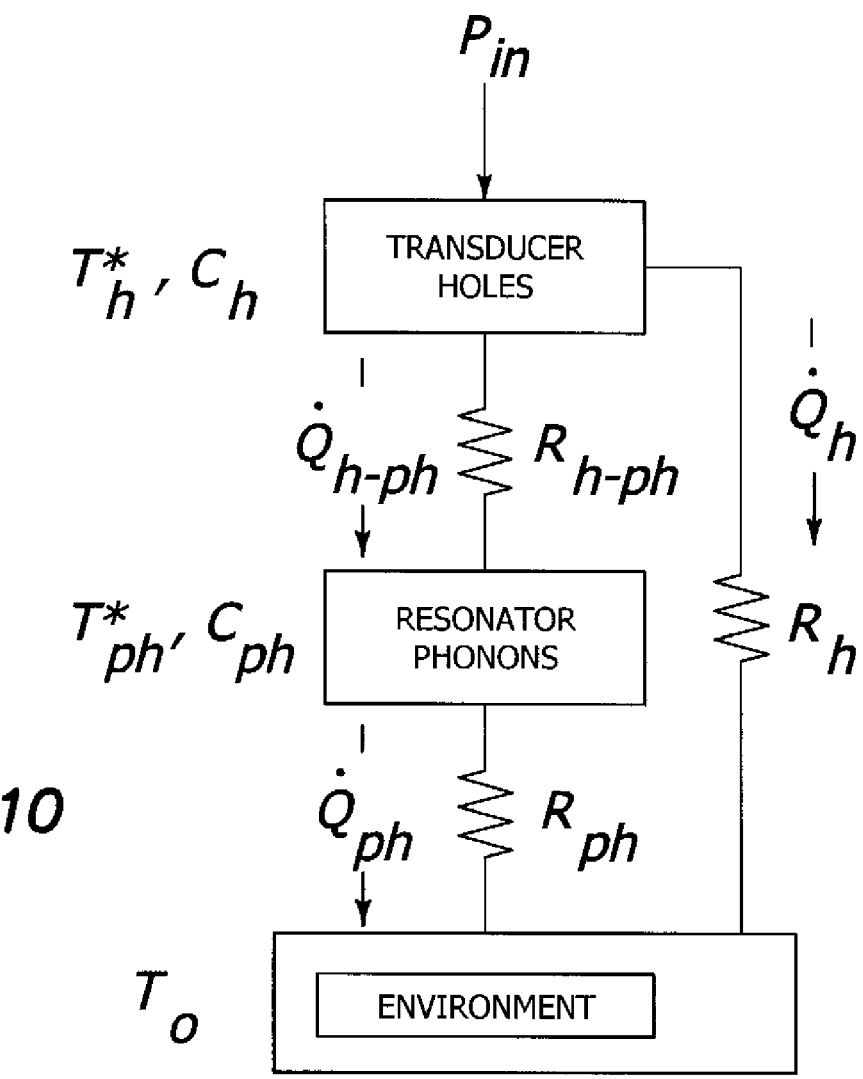
FIG. 10 is a diagram of a model for low temperature thermal transport in semiconducting piezocantilevers.

As shown in FIG. 7c fabrication begins with a bonded silicon on insulator [SOI] wafer or substrate 104 which is comprised of a 100 nm thick structural layer of undoped silicon 105, beneath which is a 750 nm sacrificial layer 107 of silicon dioxide ($SO_2$). On top of substrate 104 a 30 nm thick doped Si transducer layer 106 is epitaxially grown, which has a boron doping level of $4 \times 10^{19}/cm^3$. Above layer 106, 60 nm thick gold electrodes 108 are patterned, each with a 5 nm chromium underlayer 110 to promote adhesion. Electrodes 108 form Ohmic electrical contacts to the doped silicon epilayer 106. A membrane 112 from which the devices are subsequently patterned is created by a backside deep reactive ion etch [DRIE] to form a deep trench 114 through the substrate (75 µm×75 µm cross section). This etch is carefully terminated at the oxide layer 107 and ultimately yields the aforementioned fluidic via 102 shown in the SEM of FIG. 7a.

The wafers are then diced into individual 11 mm×11 mm dies. Prior to the nanofabrication steps the oxide layer 107 is removed from the back side of the trenches 114 using a buffered oxide etch. The cantilevers 100 are then defined by electron beam lithography, employing lift-off to pattern a 30 nm aluminum mask (not shown) that protects the active areas during the subsequent, vertical electron cyclotron resonance (ECR) plasma etch process using the gasses $NF_3$, $Cl_2$, and Ar that defines the devices. The aluminum mask is subsequently removed using a 10% potassium hydroxide solution.

These devices have a geometry that is somewhat more complex than a simple cantilever in that they are attached to the supports 27 by two small "legs" or flexures 25 which serve to concentrate both strain and current flow within the same local to enhance sensitivity as shown in FIG. 7a. FIG. 7a is a SEM image of the piezoresistive nanocantilever force sensor with thickness 130 nm, of which the topmost 30 nm comprises the p+ transducer layer. The current path flows along the two outer silicon "legs" 25; the central Au-coated Si "line" running longitudinally along the center of the cantilever 100 enables biosensing applications.

The completed devices employed in the illustrated embodiment have dimensions l=55 µm, w=7 µm, $w_{leg}$=2 µm, $l_{leg}$=5 µm. Much smaller devices than the illustrated embodiment have been patterned and this methodology has proven well-suited to fabrication at the sub-100 nm scale as well as at the illustrated micron level. Assuming end-loading and fundamental mode response, the force constant for these devices can be approximately represented as $$K_0 = \frac{El^3}{\frac{4l^3}{w} + (2l_{leg}^3 - 6ll_{leg}^2 + 6l^2 l_{leg})\left(\frac{1}{w_{leg}} - \frac{2}{w}\right)} \quad (1)$$

Assuming a Young's modulus of E=110 GPa, we deduce from Eq. (1) a value $K_0$=2.34 mN/m for the devices of this embodiment. This value is closely confirmed by finite-element numerical simulations which yield $K_0$=2.46 mN/m. The effect of the gold electrode 24 patterned along the center of the cantilever 100 has been included in these simulations. These devices are oriented so that current flow within the legs or flexures 25 occurs along the <110> direction, for which the piezoresistive coefficient, $\pi_L$ is about $4 \times 10^{-10}$ Pa$^{-1}$.

As grown, the p+ transducer layer 106 has a measured resistivity of 1 kΩ/square; an increase of about 25% was noted after processing. The total 2-terminal resistance of the device was 19.3 kΩ. This resistance comprises three contributions: 6.3 kΩ from the strain sensing leg region is 6.3 kΩ, 5.5 kΩ/leg for the resistance from the contact pad to the cantilever legs 25 (measured on a 4-terminal device of comparable geometry) and 2 kΩ from the spreading resistance at the neck of the cantilever legs 25 and the contribution from the end region 20 of the cantilever 100.

We now analyze the noise performance of these devices that, ideally, should be limited by the thermomechanical (mechanical-domain) noise of the force sensor itself. We characterize the device noise via $S_F(f)$, the force spectral density with units (force)$^2$/Hz, which is defined as the Fourier transform of the autocorrelation function of the fluctuating (time-dependent) effective force at the cantilever tip 20, where f is the frequency of vibration of cantilever 100. The "force sensitivity" is then given by $\sqrt{S^F(f)}$ (units force/(Hz)$^{1/2}$). The total r.m.s. force noise is the integral of this force sensitivity over the measurement bandwidth. The force spectral density arising from thermomechanical fluctuations, which is white over the physically relevant regime, is given by $S^\gamma_F = 4k_B T_\gamma = 4k_B T\, K_0/(2\pi Q\, f_0)$. Here γ, $f_0$, and $Q=2\pi M_0 f_0/\gamma$ are the damping coefficient (with units kg/s), fundamental mechanical resonance frequency, and quality factor, respectively, for the vibrational mode under consideration. $M_0=K_0/(2\pi f_0)$ defines the modal mass at the modal frequency. At room temperature the measured fundamental resonance frequency and quality factor are 58.1 kHz and 2000, respectively as shown in the graph of FIG. 7b where spectral density is shown as a function of frequency, hence the associated force sensitivity expected from thermomechanical fluctuations is 235 aN/√Hz. FIG. 7b is a graph of the voltage noise spectral density obtained at room temperature with a 0.3V bias, measured at the device output terminals. The two principal components evident originate from electrical-domain (Johnson) noise from the transducer itself, $S_V^J$ and piezoresistively-transduced thermomechanical fluctuations, $S_V^\gamma$. The cantilever's dynamical response function, H(f), transforms this force spectral density into the spectral density for displacement fluctuations:

$$S_x^\gamma(f) = S_F^\gamma |H(f)|^2 = S_F^\gamma \frac{1}{16\pi^4 M_0^2[(f^2 - f_0^2)^2 + (ff_0/Q)^2]} \quad (2)$$

Here x represents the coordinate of cantilever motion measured at its distal end 20.

Other "extrinsic" noise sources affect the device performance. In the absence of force stimuli, thermodynamic displacement fluctuations are transduced by the biased piezoresistors into an equivalent voltage noise at the device output terminals. In the ideal case, the transduced contribution from $S_x^\gamma(f)$ should dominate the intrinsic, electrical-domain noise of the piezoresistors arising from Nyquist and flicker-noise mechanisms. More formally, the voltage noise spectral density arising from electrically-transduced thermomechanical fluctuations is $S_V^\gamma(f)=S_x^\gamma(f)\mathfrak{R}^2(I_b)$. Here $\mathfrak{R}(I_b)=I_b(\partial R_T/\partial x)$ represents the voltage responsivity (with units V/m) characterizing the performance of the piezoresistive transducers biased with a DC current, $I_b$. The quantity $\partial R_T/\partial x$ represents the differential sensitivity of device resistance to displacement; it can be deduced empirically by fitting the electrically-transduced thermomechanical resonance peak to a Lorentzian response as illustrated in FIG. 7b, after subtracting the predominantly white background electrical noise near resonance (which we measure experimentally). For the illustrated embodiment this procedure yields $\partial R_T/\partial x$ equal to about 0.017 Ω/nm. Theoretically we expect this differential responsivity to be given by the expression $$\partial R_T/\partial x = \frac{3\beta\pi_L}{2w_{leg}l^2}(2l - l_{leg})K_0 R_T \quad (3)$$

where $R_T$ is the resistance of the "sensing region" of the device. For the illustrative two-leg devices, finite element simulations show the narrow legs are the regions that both dominate the two-terminal resistance, as well as develop the highest strain upon cantilever deflection. We estimate $R_T$ from the device geometry using the measured resistance per square for the material. β is a parameter introduced by Harley and Kenny to account for the fraction of the full strain distribution sampled by the finite-thickness piezoresistive layer. In their work β is about equal to 0.7. We also employ this value of β for our devices, which are geometrically similar. Using Eq. (3) and the measured $\partial R_T/\partial x$ from FIG. 7b, we can deduce the device gauge factor as G=$\pi_L$ E=47. This agrees quite closely with the expected value of 44. Similar results were obtained upon performing a direct measurement of the gauge factor using an AFM, which provided a calibrated displacement.

To evaluate the temperature-dependent force sensitivity of the device requires evaluation of the actual device temperature, which can be affected by bias-current-induced heating. As demonstrated below, this begins to play a significant role only at our lowest temperatures and is otherwise negligible. In this regime the electronic carriers (holes) and phonons within a device under bias are not in thermal equilibrium. For the temperature range over which experimental results are presented here ($T_0 \gtrsim 6K$, where $T_0$ is the ambient temperature) thermal conduction via hole diffusion is negligible as confirmed below. For the purpose of these calculations we therefore assume that all heat is dissipated via the phonon conduction pathway. The temperature dependence of the mechanical properties of the device is determined by the phonon temperature ($T_{ph}$). We assess this quantitatively by assuming that uniform Joule heating within the cantilever legs 25 along their length generates a one-dimensional phonon temperature profile, satisfying the expression $2tw_{leg}\kappa_{Si}(d^2T_{ph}/dy^2)=-Q/l_{leg}$. Here y=[0, $l_{leg}$], represents the position along a cantilever leg 25 measured from its anchoring support 27. We assume the thermal boundary condition at y=0 is established by the (regulated) substrate temperature; whereas at y=$l_{leg}$, the distal end 20 of the cantilever legs 25, it is established by the condition that the temperature gradient vanishes in these vacuum-based measurements. Heat loss via black-body radiation is negligible. At low temperatures the thermal conductivity of silicon, $\kappa_{Si}$, is about equal to $\kappa_{Si} \sim c_V \bar{v}_s \bar{l}/3 = \alpha_{ph} T_{ph}^3$ is estimated assuming simple diffusive thermal transport where $c_V$ is the specific heat per unit volume given by the Debye formula, $c_V(T) = [12\pi^4 k_B \rho / 5 m_{Si}](T_{ph}/T_D)^3$, $m_{Si}$ is the atomic mass of silicon, and $T_D = 645K$ is the Debye temperature for silicon. The average speed of sound for silicon given by $$\bar{v}_s = \frac{\left(\sum_{i=1}^{3} \frac{1}{v^2 i}\right)}{\left(\sum_{i=1}^{3} \frac{1}{v^2 i}\right)} \sim 5634 \text{ m/s (at '73K)},$$

'73K), where the summation is over propagation modes and the average is over propagation direction. Here $\bar{l}$ is the effective phonon mean free path. Based upon previous low temperature thermal transport studies of nanoscale beams with geometry similar to the piezoresistive legs employed here, we assume a boundary scattering limited value $\bar{l}$ about $1.12\sqrt{A}$. Here A is the cross sectional area of the beam. With these formulae we deduce the average temperature within the leg region in steady-state (under current bias) for all data taken below 40K. Above 40K the Debye formula ceases to be valid for determining thermal conductivity. However, for the full range of biases employed the illustrated embodiment we have verified that bias heating is negligible in this regime. From the thermal diffusion equation we obtain a steady-state temperature profile;

$$T_{ph}(y) = \left(\dot{Q} l_{leg} / 2 t w_{leg} \alpha_p - \beta^2 (y^2 / l_{leg}^2 - 2y/l_{leg} + 1)\right)^{\frac{1}{2}} / \beta^{\frac{1}{2}} \quad (4)$$

along the length of the piezoresistors, where $$\beta = \left((T_0^4 + 2l_{leg} \dot{Q}/t w_{leg} \alpha_p)^{\frac{1}{2}} - T_0^2\right)/2$$

and $T_0$ is the ambient temperature. We employ its longitudinally averaged value $$\langle T_{ph} \rangle = \int_0^{l_{leg}} [T_{ph}(y)/l_{leg}] dy$$

as an approximate measure of the effective device temperature in steady-state.

The cryostat-mounted sample stage was engineered such that a 1000 resistor, used for controlling the ambient temperature, passed through the center of a copper block on which the sample was mounted. Apiezon N grease was used to ensure thermal contact of the heating resistor and copper block. A silicon diode thermometer was mounted on the opposite side of the copper block at a comparable distance from the heating resistor as the micro-cantilever device. The measured temperature from this diode was used as the ambient temperature, $T_0$. The diode thermometer and heating element were controlled using a Lakeshore 340 temperature controller.

To assess the validity of the effective phonon temperature of the piezoresistive sensors calculated above, we perform two control experiments summarized in Table I.

| P = 22 µW | | | $T_0$ = 11.5 K | | |
|---|---|---|---|---|---|
| $T_0$ | $\Delta T_{meas}$ | $\Delta T_{calc}$ | P | $\Delta T_{meas}$ | $\Delta T_{calc}$ |
| 7.6 K | 13.3 K | 12.4 K | 3.4 µW | — | 4.0 K |
| 11.5 K | 10.4 K | 9.9 K | 6.9 µW | 5.9 K | 5.8 K |
| 15.0 K | 7.8 K | 8.0 K | 22 µW | 10.4 K | 9.9 K |
| 20.0 K | 4.6 K | 5.8 K | 43 µW | 12.6 K | 12.9 K |
| | | | 47 µW | 12.9 K | 13.4 K |

Figure 8A:
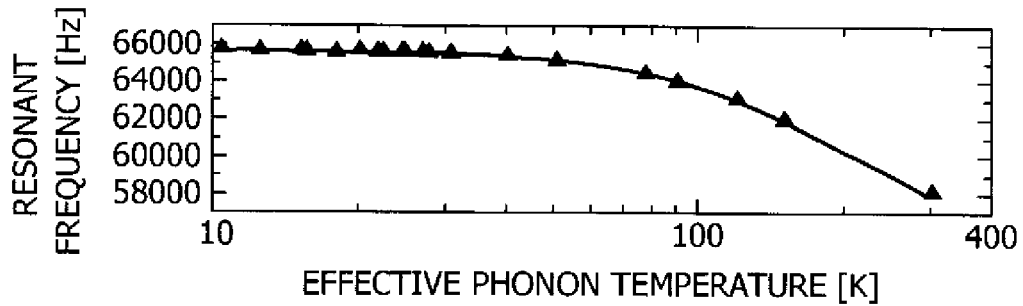
Figure 8B:
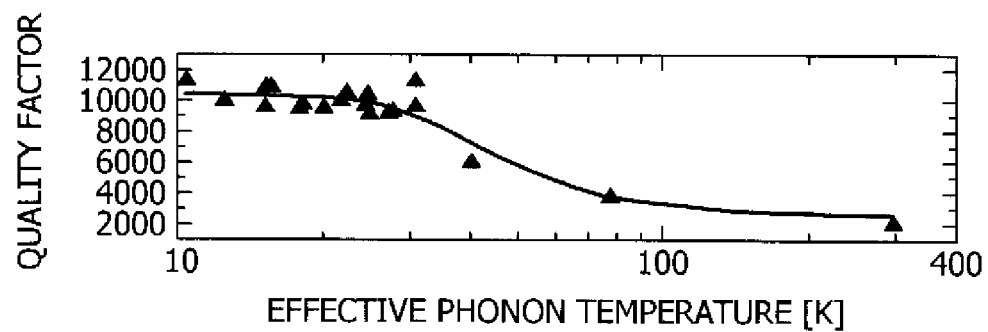
Figure 8C:
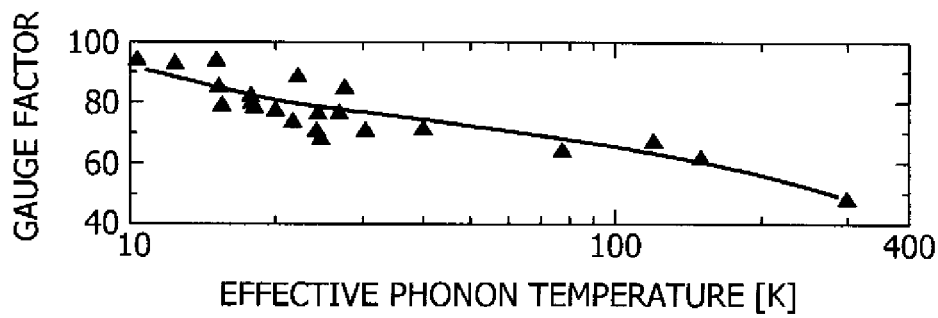
FIG. 8c is a graph showing the effective phonon temperature [K] dependent performance of the gauge factor of the nanocantilever force sensor of FIG. 7a. The data of FIGS. 8a-8c is for the thermomechanical resonance, collected at a bias of 3.3 µW. The temperature scale has been corrected to account for heating at this bias power. The solid gray lines provide a guide to the eye.
Figure 9:
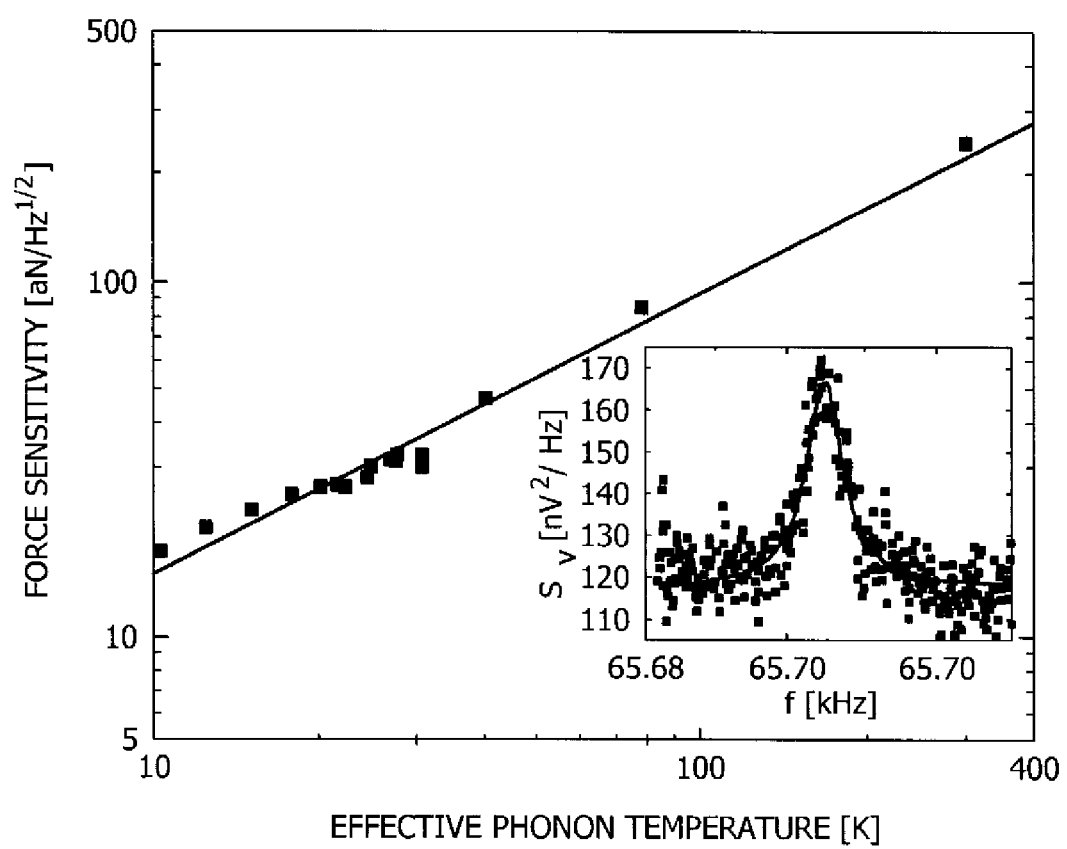
FIG. 9 is a graph of the force noise spectral density for the nanocantilever force sensor of FIG. 7a as a function of effective phonon temperature.

Table I is a summary of control experiments performed to assess the validity of the heating correction. $T_0$ is the initial temperature (before heating), $\Delta T_{meas}$ the temperature rise as determined by the resonance frequency shift (FIG. 8a), and $\Delta T_{calc}$ is the temperature rise estimated from the thermal conduction calculations discussed in this specification.

In the first, we fix the bias power and evaluate the resulting temperature rise in the sensors (piezoresistors) for various ambient (substrate) temperatures, $T_0$. This procedure involves an initial calibration of the resonant frequency versus substrate temperature,* where the hole thermal conductivity is given by the Wide-mann-Franz law $$\kappa_h = \pi^2 (k_B/e)^2 \sigma T_h / 3$$

The temperature dependence of the thermal conductivity makes solution of this differential equation non-trivial, hence we evaluate it numerically. In these equations $T_h$ represents the (local) effective steady state temperature of the holes, $t_{doped}$ represents the thickness of the conducting layer of the piezoresistor, D represents the conductivity of the piezoresistor and e is the electronic charge. The temperature profile of the phonons is determined by Eq. (4) where the heat transferred, Q is now $dQ_{ph}/dt$, the heat transferred via the phonon conduction pathway.

Once the temperature profiles for holes and phonons have been evaluated, the heat transferred from holes to phonons can be calculated using the equation $$\dot{Q}_{h-ph} = \int dV \int_{T_{ph}}^{T_h} dT G_{h-ph}(T(y))$$

where the volume integral is over the conducting region of the device and $G_{h-ph}$ is the hole-phonon thermal conductance per unit volume given by $G_{h-ph}(T) = C_h(T) \Gamma_{h-ph}(T) = g_{h-ph} T^4$ where $C_h$ is the electronic heat capacity per unit volume and $\Gamma_{h-ph}(T)$ is the hole-phonon scattering rate. We model the hole heat capacity as that of Sommerfeld free hole gas, $C_h(T) = \pi^2 p k_B T/\epsilon_F = \gamma_h T$ where p is the hole density, $\epsilon_F = (h/2\pi)^2 (3\pi^2 p)^{2/3}/2 m_h$ is the Fermi energy, and $m_h$ the (light) hole mass in the valence band. Assuming the holes and phonons are Fermi and Bose distributed, respectively, the deformation potential hole-phonon scattering rate, $\Gamma_{h-ph}$ is given by $$\Gamma_{h-ph} = \frac{3\zeta(3) k_B^3 D^2}{\pi (h/2\pi)^2 \bar{v}_S^4 v_F \rho} T^3 = \alpha_{h-ph} T^3$$

where D=8.3 eV is the deformation potential and $\zeta(3)=1.202$. The relative values for the heat conducted via the two thermal conduction pathways $\dot{Q}_h$ and $\dot{Q}_{ph}$ is not known a priori. The system is solved by iteratively until convergence is attained yielding a $\dot{Q}_h = \dot{Q}_{ph}$ (subject to the constraint $P_{in} = \dot{Q}_h + \dot{Q}_{ph}$.

Figure 11A:
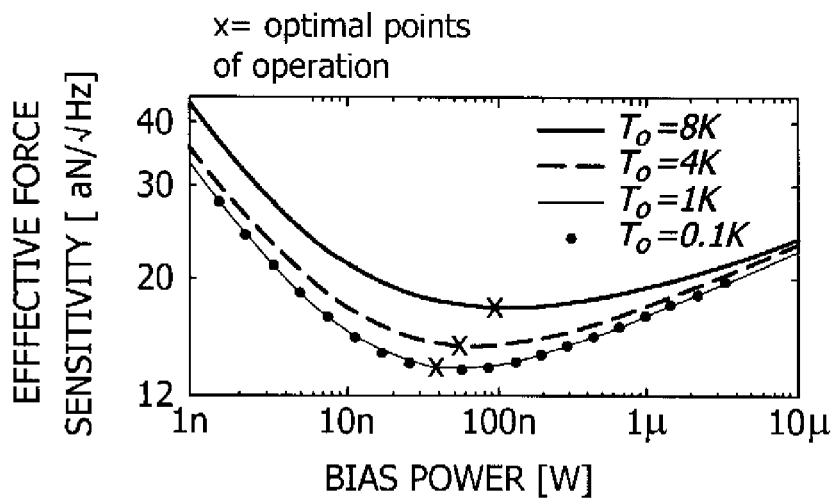
FIGS. 11a-11f are graphs which show the optimization of transduced force sensitivity for two device geometries.
Figure 11B:
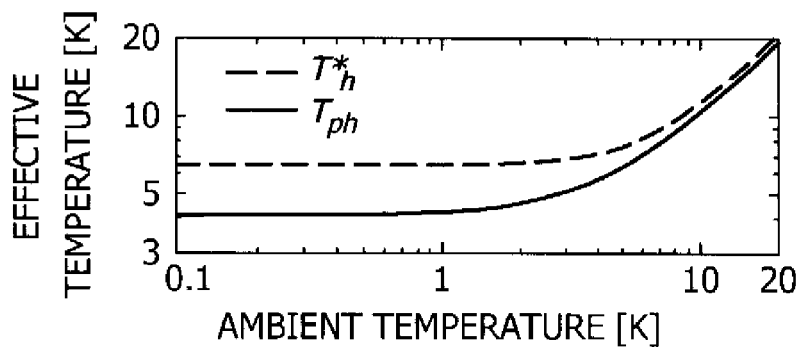
Figure 11C:
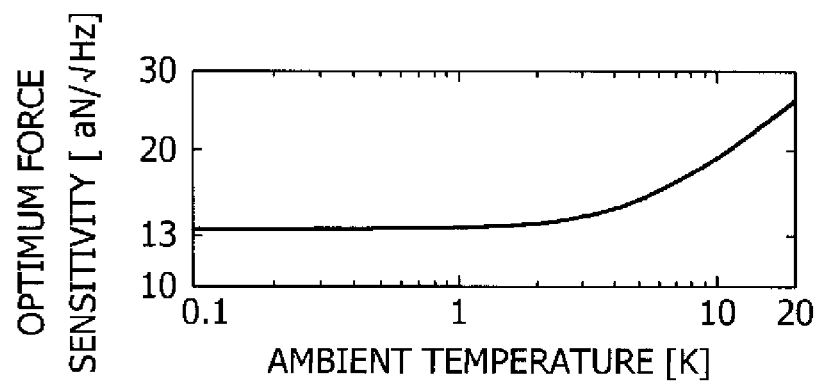
Figure 11D:
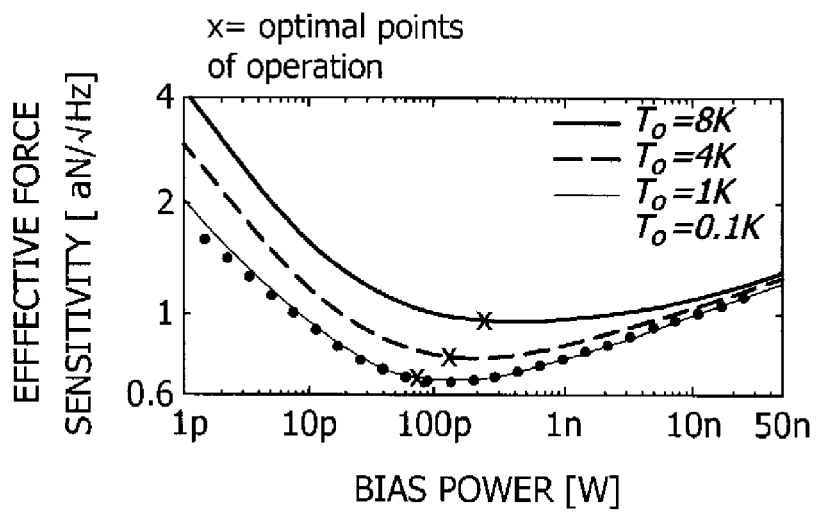
Figure 11E:
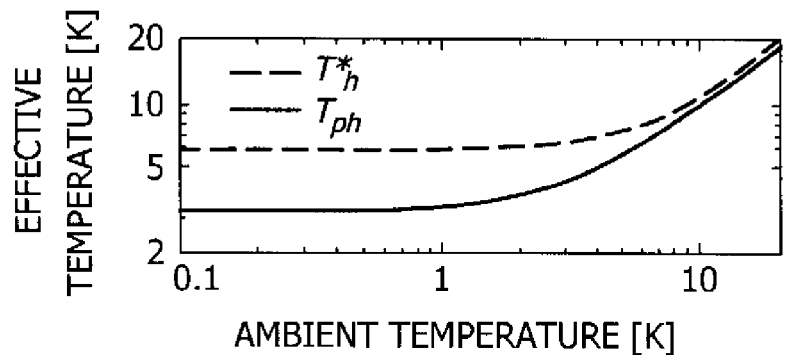
Figure 11F:
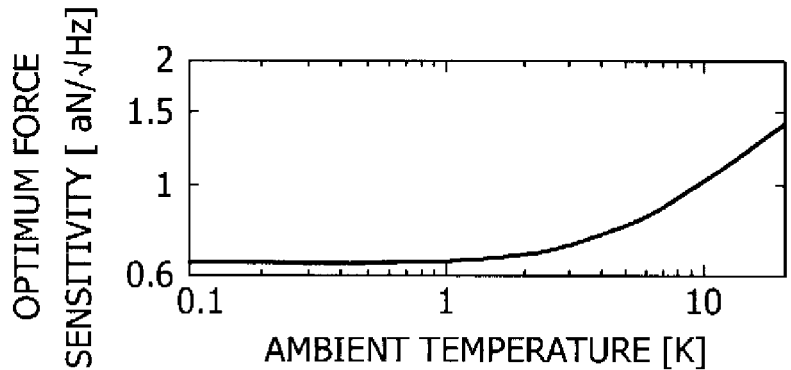

The effective, electrically-transduced force noise referred to the input (RTI) calculated with this model is shown at four different ambient temperatures in FIG. 11a for the experimental device geometry. FIGS. 11a-11f are graphs which show the optimization of transduced force sensitivity. FIGS. 11a and 11d are graphs of an evaluation of the bias power dependence of the effective force noise, which includes both mechanical- and electrical-domain contributions (referred to input). Calculated performance is displayed for two device geometries. The microdevice on which experiments were conducted is shown in the plots of FIGS. 11a-11c and a smaller, but realistic, nanodevice in the plots of FIGS. 11d-11f. At each ambient temperature, $T_0$, the minima define an optimal bias point, $P_{in}^{(opt)} = I_B^{(opt)} R_T^2$. At low bias power the responsivity of the transducer decreases, thereby leading to an increase in the effective force noise (referred to input). At high bias power the total force noise increases due to Joule heating. In FIGS. 11b and 11e at the optimal bias power the transducer hole gas and the resonator phonons attain elevated steady-state temperatures, $T^*_h$ and $T_{ph}$, which depend upon $T_{ph}$. In FIGS. 11c and 11f the optimum force sensitivity attained at $P_{in}(T_0)$, is shown as a function of $T_0$. Note that an improvement in force sensitivity of greater than an order of magnitude is observed for the nanoscale device. FIGS. 11a-11f are graphs which show the optimization of transduced force sensitivity. FIGS. 11a and 11d are graphs of an evaluation of the bias power dependence of the effective force noise, which includes both mechanical- and electrical-domain contributions (referred to input). In FIGS. 11b and 11e at the optimal bias power the transducer hole gas and the resonator phonons attain elevated steady-state temperatures, $T^*_h$ and $T_{ph}$, which depend upon $T_{ph}$. In FIGS. 11c and 11f the optimum force sensitivity attained at $P_{in}(T_0)$, is shown as a function of $T_0$. Note that an improvement in force sensitivity of greater than an order of magnitude is observed for the nanoscale device.

For very low bias currents the total force noise increases due to the smaller transducer responsivity and consequently the dominance of $S_F^J$ (RTI). At high bias currents, the total noise increases due to the increased device temperature. It is clear that by minimizing Eq. (5) we can determine the optimum bias power, $P_{in}$ yielding the highest sensitivity for a given ambient temperature and device geometry. The effective temperature of both the phonons and holes is shown in FIG. 11b. It is evident that below a few degrees Kelvin, the Joule heating is very significant in determining the effective device temperature. The temperature dependence of the optimum force sensitivity obtained by this procedure is shown in FIG. 11c for the experimental geometry. The corresponding effective temperatures for the holes and phonons are shown in FIG. 11b. As seen, a limiting sensitivity of $\sqrt{S_F}$=13 aN/√Hz can be achieved for an ambient temperature $T_0$<1K.

This analysis allows us to assess the sensitivity improvements possible through optimization of geometry, for example, by reducing the width of the cantilever legs 25 and decreasing the total device thickness. To illustrate the improvements that are easily within the scope of our present, top-down nanofabrication capabilities, we consider nanocantilever devices with $w_{leg}$=100 nm, w=300 nm, t=30 nm, $t_{doped}$=7 nm, $l_{leg}$=1 µm and otherwise identical to the device of FIG. 7a. For such a device one obtains an optimal sensitivity $\sqrt{S_F}$=0.6 aN/√Hz for T, <1K. A quality factor of 10000 was assumed for this device. This seems reasonable based on a survey of work that has gone on in the field. The optimum sensitivity versus ambient temperature is shown in FIG. 11f.

In the analysis of our experimental data we asserted that thermal conduction via holes was not significant in the temperature range studied. We revisit that assertion here. The lowest temperature of data collection was at an ambient temperature of 6.0K with a bias power of 1 µW. Under the assumption that the power was dissipated entirely via the phonon conduction pathway, an average phonon temperature of 10.3K was calculated. Based on this phonon temperature and 1 µW of power transfer we obtain an effective average hole temperature of 12.8K. The heat dissipated via hole diffusion at this effective hole temperature, estimated using the Wiedemam-Franz law, $\dot{Q}_{p-ph} \sim 2\pi^2 (k_B/e)^2/3R_T(\langle T_h \rangle^2 - \langle T_0 \rangle^2)$ is of order 1 nW and therefore negligible compared to the 1 µW dissipated via phonon conduction.

In summary, the illustrated embodiment presented here thus elucidate the ultimate, practical limits for self-sensing displacement transduction by means of semiconducting piezoresistors. We have experimentally demonstrated the attainment of a force noise floor at the level of 17 aN/√Hz at about 10K, a milestone for self-sensing devices. Furthermore, our analysis establishes that sub-aN/√Hz sensitivity is attainable by scaling the cantilever dimensions downward into a regime that is readily attainable by top-down methods. Our analysis also elucidates, for the first time, the existence of a temperature- and geometry-dependent optimum bias current at which the force sensitivity is maximized. This analysis shows that heating effects in micro- and nanoscale piezoresistive devices become substantial for ambient temperatures below 1K. This would appear to preclude attainment of quantum-limited force sensitivity at temperatures $T_0 < \hbar \omega_0 / 2\pi k_B$ where the resonant mode becomes thermally depopulated, but otherwise clearly enables a wide range of applications requiring compact, and integrated high frequency force sensing with unprecedented sensitivity.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following invention and its various embodiments.

Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations. A teaching that two elements are combined in a claimed combination is further to be understood as also allowing for a claimed combination in which the two elements are not combined with each other, but may be used alone or combined in other combinations. The excision of any disclosed element of the invention is explicitly contemplated as within the scope of the invention.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. An apparatus for detecting the presence of a biomolecule comprising:
    at least one self-sensing micro or nanocantilever having a movable distal end; and
    at least one rigid dock adjacent to the distal end which dock remains stationary under global actuation, the rigid dock and the distal end arranged and configured to bind to the biomolecule extending between the distal end and the rigid dock and across a gap less than 100 nanometers wide disposed there between, and
    wherein the rigid dock comprises a notch defined into its surface to accommodate the distal end of the micro or nanocantilever and the gap disposed circumferentially around the distal end.

2. The apparatus of claim 1 further comprising at least two substantially identical self-sensing micro or nanocantilevers each having a movable distal end and a rigid dock adjacent to corresponding distal ends, one of the at least two distal ends arranged and configured to bind to the biomolecule extending between the one distal end and the rigid dock and across a gap less than 100 nanometers wide disposed there between,
    wherein the rigid dock comprises at least two notches defined into its surface to accommodate the distal end of the at least two micro or nanocantilevers and the gaps disposed circumferentially around each of theft distal ends; and
    a piezoresistive differential detector coupled to the at least two self-sensing micro or nanocantilevers to provide an output signal with common mode rejection.

3. The apparatus of claim 1 further comprising a remote actuator of the at least one self-sensing micro or nanocantilevers.

4. The apparatus of claim 3 further comprising a plurality of self-sensing micro or nanocantilevers and a plurality of notches defined in the rigid dock, the plurality of self-sensing micro or nanocantilevers and the plurality of notches combined as a plurality of suites and arranged into an array of suites with a plurality of rigid docks.

5. The apparatus of claim 1 where the self-sensing micro or nanocantilever incorporates a semiconductor piezoresistor as a self-sensing transducer of motion of the micro or nanocantilevers, and further comprising a cryogenic environment in which the apparatus is maintained.

* * * * *